United States Patent [19]  [11] 3,930,946
Maldonado et al.  [45] Jan. 6, 1976

[54] YEASTS

[75] Inventors: Paul Maldonado, Chatou; Jean-Pierre Desmarquest; Claude Gaillardin, both of Paris; Daniel Binet, Rueil Malmaison, all of France

[73] Assignees: Institut Francaise du Petrole, des Carburants et Lubrifiants, Paris; Institut Francais du Petrole, Rueil-Malmaison, both of France

[22] Filed: Nov. 26, 1973

[21] Appl. No.: 418,838

[30] Foreign Application Priority Data
Nov. 24, 1972 France .............................. 72.41913

[52] U.S. Cl. ................................. 195/28 R; 195/78
[51] Int. Cl.² ......................................... C12B 1/00
[58] Field of Search .......... 195/28 R, 36 R, 82, 112, 195/115, 78

[56] References Cited
UNITED STATES PATENTS
3,616,213   10/1971   Tsugawa ........................... 195/28 R

*Primary Examiner*—A. Louis Monacell
*Assistant Examiner*—R. B. Penland

[57] ABSTRACT

A process for the preparation of a stable diploid of *Candida lipolytica* which comprises (a) in a first stage, separately cultivating two haploid strains of *Candida lipolytica* of opposed sign in a medium rich in assimilable carbon nutrient; (b) in a second stage, cultivating the two resultant strains together in a medium poor in assimilable carbon nutrient; and (c) in a third stage, after the appearance of diploid colonies, treating them with a mutagenic agent to stabilize them. The invention also comprises a process for the preparation of α-ketoglutaric acid which comprises cultivating a diploid strain obtained by crossing two *Candida lipolytica* haploid strains of opposite sign in a medium containing, as source of assimilable carbon, at least one hydrocarbon.

6 Claims, No Drawings

YEASTS

This invention is concerned with the preparation of new strains of yeasts and the use thereof in the preparation of α-ketoglutaric acid by fermentation.

The use of yeasts in fermentation processes is well known, either to produce a biomass for use in or as a feed stuff or for the production, together with a biomass, of excretion products such as, for example, α-ketoglutaric acid. The various fermentations processes employ, as nutrients, carbohydrates, fatty acids, alcohols, or hydrocarbons. For any particular fermentation process an attempt is made to select the best strain of the yeast. Thus the strains are isolated from soil or water samples and then tested in a number of ways to ascertain their capacity for assimilating the chosen nutrient, their rate of growth and their ability to produce the desired metabolite.

In a detailed study of certain yeasts, especially yeasts of the species *Candida lipolytica* which is already known to ferment on hydrocarbon substrates, there was found, following Wickerham et al. (Science 167, 1141 (1970),) that the possibility of genetic combinations between haploid strains of opposite sign, combinations which imply the, at least transitory, formation of a diploid state. In contradistinction to Wickerham et al., who observed only the sporulation of such combinations followed by the formation of haploid descendants, it has now been found possible to isolate the diploids and to stabalize them.

Accordingly, it is one object of the present invention to provide a process for the preparation of stable diploids from haploid strains of opposed genetic sign. According to the invention, therefore, there is provided a process for the preparation of a stable diploid of *Candida lipolytica* which comprises (a) in a first stage, separately cultivating two haploid strains of *Candida lipolytica* of opposed sign in a medium rich in assimilable carbon nutrient; (b) in a second stage, cultivating the two resultant strains together in a medium poor in assimilable nutrient; and (c) in a third stage, after the appearance of diploid colonies, treating them with a mutagenic agent to stabilize them.

In the process of the invention, conventional media are used for the culture of the haploid of diploid strains of *Candida lipolytica*. Such media contain a source of assimilable carbon which may be a hydrocarbon or a mixture of hydrocarbons, or a carbohydrate, molasses or sugar, for example glucose. The culture media also contain a source of nitrogen which will generally be, for example, an ammonium salt, a chloride or a nitrate. The culture medium any also contain a sufficient amount of a yeast extract or dried yeast which acts as a source of co-factors, such as vitamins, mineral salts or amino acids, all of which are of use in the growth of the strains. The mineral salts are commonly salts of iron, copper, magnesium or the like.

It is intended that the medium rich in carbon source shall contain at least 10 grams per liter of assimilable carbon source and that the medium poor in assimilable carbon will contain about twenty times less of such source than the rich medium. The values given above are, of course, approximate, since the amount of concentration of the carbon source will vary continually as the yeast assimilates the carbon. In accordance with a preferred embodiment of the invention, the rich medium will contain about 20 grams per liter of the assimilable carbon source, the concentration of which will decrease with the growth of the yeast. The carbon-poor source will thus have an assimilable carbon nutrient content of for example, between 2 and 0.5 grams per liter. The cultivation in the two first stages of the process of the invention will generally be carried out at a temperature of from 5° to 35°C, preferably, for the best growth, between 20° and 35°C. The second stage is advantageously carried out at a temperature lower than that at which the first stage is carried out, thus the first stage is most preferably carried out at a temperature of from 25° to 35°C and the second stage at a temperature of 20° to 25°C.

The culture medium in the two stages will generally have a slightly acid pH, that is a pH of from 2 to 7, preferably from 5 to 7. If during the course of the cultivation the pH becomes too acid, it may be brought back to its original value by the addition of a base such as potassium hydroxide. The two first stages may be carried out using a solid or a liquid culture medium; the compositions of the media being similar except for the use of a solidification agent, such as a Bacto Agar Difco in the case of the solid media.

In the third stage of the process of the invention, the diploids are stabilized by mutagenesis. Mutagenesis may be achieved using a chemical mutagenic agent or by irradiation. Thus, for example, chemical mutagenic agents which may be employed are NMU (nitrosomethylurethane,) or NMG (nitrosomethylguanidine); whereas suitable irradiant mutagenic agents are X-rays or ultra violet radiation.

In a modification of the invention, after the second stage, the culture is replaced in a carbon-rich medium which facilitates the growth of the haploid and diploid strains, before stabilization by mutagenesis. This modification makes it possible to avoid sporulation of the diploids obtained. In accordance with another modification of the invention, before stabilization, the colonies of the diploid cells are separated from the other colonies and this makes it possible to obtain a good cellular density of *Candida lipolytica* diploids and leads to advantages when they are used in fermentation of processes.

The diploids obtained, as will be described below, have a higher ADN content than the parent strains, and they also have a greater size which is advantageous when it comes to the recovery of the cellules and their separation from the medium.

It has also been found, in accordance with the invention, that the diploid strains have, as compared with the parent strains, improved fermentation properties both as regards rate of growth and ability to produce metabolites. It is, accordingly, another object of this invention an improved fermentation process using the diploids in which not only is the recovery of the cellules facilitated in view of their greater size but also are there obtained greater quantities of the desired metabolites than in the case of a fermentation process using the haploid strains.

Accordingly, the invention also provides a process for the preparation of alpha-ketoglutaric acid which comprises cultivating a diploid strain obtained by crossing two *Candida lipolytica* haploid strains of opposite sign, in a medium containing, as source of assimilable carbon at least one hydrocarbon.

The source of assimilable carbon used in the fermentation process of the invention, may, as described above for the cultivation process, be a carbohydrate or a hydrocarbon. A particular advantage of the invention lies in the possibility of using a hydrocarbon source which preferably comprises a paraffinic hydrocarbon which may be a single n-paraffin or an n-paraffinic cut. Whilst the use of a single n-paraffin makes it possible to obtain the best results it is generally preferred, basically on grounds of cost, to use an n-paraffinic cut containing paraffins containing from 9 to 22 carbon atoms per molecule. The culture medium will also contain, beside the carbon source, the usual nutrients required for a fermentation for the production of alpha-ketoglutaric acid, namely a source of nitrogen, such as that used in the cultivation process as described above, and various metal salts such as salts of iron, magnesium, zinc, potassium, sodium etc. The fermentation is generally carried out at a temperature of 25° to 35°C pH of between 2 and 7, preferably between 2.5 and 5.0. During the fermentation, organic acids are formed in the culture, thereby causing the pH to reduce, and the pH may be maintained at its optimum value by the controlled addition of a base, such as, for example, ammonia.

The fermentation is suitably carried out continuously in the presence of air and the culture medium should be preferably be strongly stirred or agitated, by any suitable means, in order to obtain the best possible dispersion of the hydrocarbonaceous nutrient.

Before commencing the fermentation proper the diploid strains of *Candida lipolytica* may be precultured in order to grow the yeast, which makes it possible to seed the fermentor with an adequate similar concentration (for example $10^7$ cellules per ml). The preculture medium will comprise the nutrients of the fermentation medium to which has been added, preferably, a small amount of thiamine hydrochloride (vitamin $B_1$). This nutrient is only present in the preculture medium since it is favourable to the growth of the yeasts but is unfavourable to the production of the metabolites.

In order that the invention may be well understood the following examples are given by way of illustration only.

EXAMPLE 1

Two strains of *Candida lipolytica* isolated from soil samples were used, namely a haploid of sign A (IFP 29) and a haploid of sign B (ELF 30).

STAGE 1

The two strains were separately cultivated for 24 hours at 25°C on presporulation medium A (carbon-rich medium) having the following composition:

| | |
|---|---|
| Glucose | 20 g |
| $(NH_4)_2SO_4$ | 2 g |
| $KH_2PO_4$ | 2 g |
| Yeast Extract | 10 g |
| Bacto Agar Difco | 20 g |
| Distilled Water | 1000 ml |

STAGE 2

A suspension containing $10^7$ to $10^8$ cellules per milli-liter in distilled water was prepared for each of the strains. One milli-liter of each suspension was then taken and mixed together vigorously 0.1 milli-liter of the resultant mixture was then placed in a gelose 2 tube lined with sporulation medium B derived from vegetable juices and prepared as follows. 350 Milli-liters of bouillon of eight different vegetables and having an energy equivalent of about 2 grams per liter of glucose were adjusted to pH 6.8 with 1 Normal KOH solution. 7 Grams of dried IFP 29 yeast were then added to the bouillon and the whole maintained for 20 minutes at 100° on a water bath and then filtered through filter paper. The pH of the filtrate was adjusted to 6.8, as described above, and its volume doubled by the addition of an equal volume of town water. After the addition of bacto agar difco (2%) the medium was sterilized in 10 cc tubes for 15 minutes at 110°C.

The culture on medium B, where several asci were forming, was suspended in 10 milli-liters of soda-containing distilled water using a Mullard MSE disintegrator for 3 minutes at 0°C. The suspension was then spread onto medium B contained in Petri dishes at the appropriate dilution. After 7 to 15 days several diploid colonies appeared on the medium. These colonies were very rich in asci (about 50% as compared with vegetative cellules). The colonies were taken up and sorted out onto a medium rich in yeast extract (yeast extract 0.5%, glucose 2%, agar difco 2%). The large selected colonies were diploids, cultivatable as such without sporulation on complete or rich medium, over several transplants. The diploid strain obtained was called $D_{18}$.

Starting from diploid $D_{18}$ (IPF 29, ELF 30), a series of colonies were isolated after UV mutagenesis ($10^7$ cellules of $D_{18}$ irradiated for one minute at 2000 ergs/mm²/mn. All these colonies had a much reduced fertility. Starting from these colonies four strains derived from $D_{18}$ were selected which, after fifteen days and three weeks on carbon-poor medium B, no longer formed Asci (absence of sporulation). These strains were respectively designated D 1802, D 1805, D 1806 and D 1807.

It was ascertained, by ADM dosage according to the method of Burton (Biochemical Journal 62, 315-323, 1956) and by micrometric measurement of the cell sizes, that the strains remained close to the $D_{18}$.

| Characteristics of haploids and diploids | |
|---|---|
| Strain | µg of desoxyadenoisine per $10^8$ cellules |
| IFP 29 | 0.58 |
| ELF 30 | 0.65 |
| D 18 | 0.89 |
| D 1802 | 0.88 |
| D 1805 | 1.05 |
| D 1806 | 1.27 |
| D 1807 | 1.26 |

The cells were in the form of ellipsoids having the following axes.

| Strain | major axis (µ) | minor axis (µ) |
|---|---|---|
| IFP 29 | 4.5 | 2.7 |
| ELF 30 | 4.6 | 2.9 |
| D 18 | 7.7 | 4.2 |
| D 1802 | 7.8 | 2.9 |
| D 1805 | 12.1 | 6.3 |
| D 1806 | 8.3 | 4.4 |
| D 1807 | 11.3 | 5.0 |

FORM OF COLONIES ON HYDROCARBONACEOUS MEDIUM

Round, bomb shaped, granulated, brilliant, pale yellow.

| Assimilation of substrates (identical for all strains). | |
|---|---|
| Sucrose | −negative |
| Maltose | −negative |
| Galactose | −negative |
| Glucose | +positive |
| Raffinose | feeble |
| Paraffins | positive |

EXAMPLE 2

Each of the above *Candida lipolytica* strains was transplanted and incubated for 15 hours at 30°C in sterile tubes containing a gelose medium having the following composition:

| | |
|---|---|
| Yeast Extract | 0.05 g |
| Paraffin cut $C_{13}$–$C_{18}$ | 0.05 ml |
| Bacto Agar Difco | 0.15 g |
| Distilled Water | 10 ml |

Each of the resultant cultivated materials were then seeded into Fermbach flasks containing 100 ml. of a preculture medium having the following composition:

| | |
|---|---|
| Paraffin cut $C_{13}$–$C_{18}$ | 2% |
| Ammonium Nitrate | 1.8% |
| Acid Potassium Phosphate | 0.2% |
| $MgSO_4 \cdot 7H_2O$ | 0.1% |
| $FeSO_4 \cdot 7H_2O$ | 0.01% |
| $ZnSO_4 \cdot 7H_2O$ | 0.002% |
| $CuSO_4 \cdot 5H_2O$ | 0.002% |
| Thiamine hydrochloride | 6 μg |
| Thiamine | 6 μg |
| CaCO | 1 % |
| Distilled water | 100 ml |

After incubation for 48 hours at 30°C on a shaking table turning at 170 turns/minute, each of the precultures was seeded into a fermentor having a total capacitor of 4 liters and containing 2 liters of a sterile medium having the following composition:

| | |
|---|---|
| Nitrate Ammonium | 1.8% |
| Acid potassium Phosphate | 0.2% |
| $MgSO_4 \cdot 7H_2O$ | 0.1% |
| $FeSO_4 \cdot 7H_2O$ | 0.01% |
| $ZnSO_4 \cdot 7H_2O$ | 0.002% |
| $CuSO_4 \cdot 5H_2O$ | 0.002% |
| Distilled Water | 2000 ml. | n-paraffinic substrate ($C_{13}$–$C_{18}$ cut) was introduced into the fermentor at a rate of 2.5 ml. per hour and the fermentation medium was mechanically stirred at 1800 rpm, at a temperature of 31.5°C and aerated with sterile air at a flow rate of 0.2 liters of air per minute per liter of medium. The pH of the medium was maintained at 3.5 by the controlled addition of 2.5 normal aqueous ammonia. The total amount of hydrocarbon added during the culture was 208 ml. (8% by weight). 10 ml samples were taken from the fermentation medium at predetermined intervals and tested, according to the method of Friedman (Methods in Enzmology Vol. III, 414-418, Acad. Press. (1957)), to determine the α-ketoglutaric acid concentration.

The following table shows the results obtained at the end of 110 hours culture and compares the performances of the non sporulant diploid strains D 1802, D 1805, D 1806 and D 1807 with those of the parent haploid strains IFP 29 and ELF 30.

| Example | Strain | Alpha-ketoglutaric acid (g/l) |
|---|---|---|
| 2 | D 1802 | 64.5 |
| 3 | D 1805 | 66.5 |
| 4 | D 1806 | 52.3 |
| 5 | D 1807 | 52.5 |
| 6 | IFP 29 | 29 |
| 7 | ELF 30 | 31.5 |

A study of the results given in the above table shows that the yields of α-ketoglutaric acid resulting from the use of the diploids of the invention are good, not only as compared to those obtained with the parent strains, but equally very much better than those obtained in other strains of the same genus.

Further, the production of α-ketoglutaric acid using diploid strains D 1805 was carried on for more than 110 hours. The amounts of α-ketoglutaric acid produced at the rate of the production of the acid were ascertained for various culture times and the results are shown in the following table.

| Hours | α-ketoglutaric acid (g/l) | Rate of formation (g/l) |
|---|---|---|
| 110 | 65 | 1.0 |
| 160 | 113 | 0.96 |
| 240 | 185 | 0.9 |

It will be noted that the rate of formation at the time of termination of the fermentation, namely after the 240th hour, is only very slightly decreased as compared to that determined at the 110th hour; further the yield, based on the amount of hydrocarbon consumed, is always very high. These tests show that production of α-ketoglutaric acid in accordance with the invention maybe carried out for long periods of time under favourable conditions.

After the end of the culture the biomass is centrifuged. The supernatant phase is made alkali to a pH of 8.5 by the addition of powdered soda lime thereby precipitating calcium α-ketoglutaric which is recovered by filtration.

α-ketoglutaric acid is obtained by hydrolysis of the calcium salt with aqueous sulphuric acid followed by removal by filtration of the calcium sulphate and crystallisation of the acid from the filtrate concentrated under vacuum.

We claim:

1. A process for the preparation of a stable diploid of *Candida lipolytica* which comprises (a) in a first stage, separately cultivating two haploid strains of *Candida lipolytica* of opposed sign in a medium rich in assimilable carbon nutrient; (b) in a second stage, cultivating the two resultant strains together in a medium poor in assimilable carbon nutrient; and (c) in a third stage, after the appearance of diploid colonies, treating them with a mutagenic agent to stabilize them.

2. A process as claimed in claim 1 in which the carbon-rich medium contains at least 10 grams per liter of assimilable carbon nutrient.

3. A process as claimed in claim 1 in which the carbon-rich medium contains about 20 times as much assimilable carbon source as does the carbon-poor medium.

4. A process as claimed in claim 1 in which the culture media contain yeast extract or yeast.

5. A process for the preparation of α-ketoglutaric acid which comprises cultivating a stable diploid mutant of *Candida lipolytica* on a hydrocarbon substrate to produce α-ketoglutaric acid, said stable diploid being produced by (a) in a first stage, separately cultivating two haploid strains of *Candida lipolytica* of opposed sign in a medium rich in assimilable carbon nutrient; (b) in a second stage, cultivating the two resultant strains together in a medium poor in assimilable carbon nutrient; and (c) in a third stage, after the appearance of diploid colonies, treating them with a mutagenic agent to stabilize them, and finally recovering the α-ketoglutaric acid so produced.

6. A process as claimed in claim 5 in which the assimilable source comprises at least one n-paraffin containing from 9 to 22 carbon atoms.

* * * * *

UNITED STATES PATENT AND TRADEMARK OFFICE
CERTIFICATE OF CORRECTION

PATENT NO. : 3,930,946
DATED : January 6, 1976
INVENTOR(S) : Maldonado et al

It is certified that error appears in the above-identified patent and that said Letters Patent are hereby corrected as shown below:

Assignee: delete "Institute Francais du Petrol, des Carburants et Lubrifints et Entreprise de Recherches et d'Activities Petrolieres Elf, Paris Rueil Malmaison, France"

and insert --Institute Francais du Petrole et Entreprise de Recherches et d, Activites Petrolieres E.R.A.P., Rueil-Malmaison Paris, France--

Signed and Sealed this

Twenty-first Day of March 1978

[SEAL]

Attest:

RUTH C. MASON
Attesting Officer

LUTRELLE F. PARKER
Acting Commissioner of Patents and Trademarks